(12) United States Patent
Payne

(10) Patent No.: US 10,172,639 B2
(45) Date of Patent: Jan. 8, 2019

(54) DEVICES AND METHODS FOR PROTECTING AN INTERNAL CHANNEL OF A SUBJECT

(71) Applicant: UNIVERSITY OF VIRGINIA, Charlottesville, VA (US)

(72) Inventor: Spencer C. Payne, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 457 days.

(21) Appl. No.: 14/428,990

(22) PCT Filed: Sep. 26, 2013

(86) PCT No.: PCT/US2013/061926
§ 371 (c)(1),
(2) Date: Mar. 18, 2015

(87) PCT Pub. No.: WO2014/052595
PCT Pub. Date: Apr. 3, 2014

(65) Prior Publication Data
US 2015/0209074 A1 Jul. 30, 2015

Related U.S. Application Data

(60) Provisional application No. 61/705,851, filed on Sep. 26, 2012.

(51) Int. Cl.
A61B 17/34 (2006.01)
A61B 17/24 (2006.01)
(Continued)

(52) U.S. Cl.
CPC ...... *A61B 17/3423* (2013.01); *A61B 1/00154* (2013.01); *A61B 17/0218* (2013.01);
(Continued)

(58) Field of Classification Search
CPC . A61B 17/24; A61B 17/3439; A61B 17/3423; A61B 17/0218;
(Continued)

(56) References Cited

U.S. PATENT DOCUMENTS 3,568,678 A 3/1971 Pourquier
4,327,735 A * 5/1982 Hampson ........... A61M 25/0111
604/171

(Continued)

OTHER PUBLICATIONS

International Preliminary Report on Patentability in related PCT Application No. PCT/US2013/061926, dated Mar. 31, 2015.
(Continued)

*Primary Examiner* — Jocelin Tanner
(74) *Attorney, Agent, or Firm* — Meunier Carlin & Curfman LLC

(57) ABSTRACT

Devices and methods for protecting an internal channel of a subject are disclosed. In one example embodiment, a device for protecting an internal channel of a subject includes a first end portion having a first diameter and defining a first opening, and a second end portion opposite the first end portion having a second diameter and defining a second opening that is in communication with the first opening. A body portion is defined between the first end portion and second end portion. The body portion defines an interior passage between the first opening and second opening, and is expandable along a longitudinal axis from a collapsed state to an expanded state.

26 Claims, 6 Drawing Sheets

(51) Int. Cl.
*A61B 1/00* (2006.01)
*A61B 17/02* (2006.01)
*A61B 17/00* (2006.01)
*A61B 90/40* (2016.01)
*A61B 90/00* (2016.01)

(52) U.S. Cl.
CPC .......... *A61B 17/24* (2013.01); *A61B 17/3439* (2013.01); *A61B 90/40* (2016.02); *A61B 2017/00278* (2013.01); *A61B 2017/0225* (2013.01); *A61B 2017/246* (2013.01); *A61B 2017/345* (2013.01); *A61B 2017/3429* (2013.01); *A61B 2017/3443* (2013.01); *A61B 2017/3445* (2013.01); *A61B 2090/08021* (2016.02)

(58) Field of Classification Search
CPC .......... A61B 2017/00296; A61B 2017/00278; A61B 2017/3443; A61B 2017/3429; A61B 2017/0225; A61B 2017/345; A61B 2017/3445; A61B 2017/248; A61B 2017/246; A61B 90/40; A61B 1/00154
See application file for complete search history.

(56) References Cited

U.S. PATENT DOCUMENTS

| | | | | |
|---|---|---|---|---|
| 5,571,172 | A | * | 11/1996 | Chin .................. A61F 2/07 128/898 |
| 6,001,117 | A | * | 12/1999 | Huxel ................ A61F 2/04 606/191 |
| 8,100,933 | B2 | | 1/2012 | Becker |
| 8,146,400 | B2 | | 4/2012 | Goldfarb et al. |
| 2004/0019359 | A1 | | 1/2004 | Worley et al. |
| 2004/0260246 | A1 | | 12/2004 | Desmond |
| 2007/0244542 | A1 | * | 10/2007 | Greenan ............. A61F 2/07 623/1.13 |
| 2007/0244547 | A1 | * | 10/2007 | Greenan ............. A61F 2/07 623/1.35 |
| 2011/0118551 | A1 | | 5/2011 | Ciporen et al. |
| 2012/0203069 | A1 | * | 8/2012 | Hannaford ......... A61B 17/3423 600/201 |
| 2013/0204092 | A1 | * | 8/2013 | Hannaford ......... A61B 17/0231 600/236 |

OTHER PUBLICATIONS

International Search Report in related PCT Application No. PCT/US2013/061926, dated Mar. 18, 2014.

* cited by examiner

DEVICES AND METHODS FOR PROTECTING AN INTERNAL CHANNEL OF A SUBJECT

CROSS-REFERENCE TO RELATED PATENT APPLICATION

This application is a United States National Stage Application of, and claims the benefit pursuant to 35 U.S.C. § 371 of, International Patent Application Serial No. PCT/US2013/061926, filed on Sep. 26, 2013, which claims priority to and the benefit under 35 U.S.C. § 119(e) of U.S. Provisional Patent Application Ser. No. 61/705,851, filed Sep. 26, 2012 and entitled "Nasal EndoSheath Device and Related Method," by Spencer C. Payne, the contents of both of which are is incorporated herein by reference in their entireties.

BACKGROUND

Transnasal medical procedures often require instruments to be blindly passed through bilateral nasal cavities of a patient, which exposes the nasal mucosa to inadvertent damage that can result in post-operative scarring and congestion. It is with respect to these and other considerations that the various embodiments described below are presented.

SUMMARY

The present disclosure relates to devices and methods for protecting an internal channel of a subject during a medical procedure. According to some example embodiments described herein, a protective device is used to line internal portions of the nose of a human subject during a transnasal medical procedure at the skull base, for example a transphenoidal surgical procedure, such that instruments can be easily passed through the nostril to the surgical site without causing inadvertent damage to nasal passages and cavities.

In one aspect, the present disclosure relates to a device for protecting an internal channel of a subject. In one example embodiment, the device includes a first end portion, having a first diameter, that defines a first opening, and a second end portion, opposite the first end portion, having a second diameter and defining a second opening that is in communication with the first opening. The device also includes a body portion, defined between the first end portion and second end portion, which defines an interior passage between the first opening and second opening. The body portion is expandable, along a longitudinal axis, from a collapsed state to an expanded state.

In another aspect, the present disclosure relates to a method for protecting an internal channel of a subject. In one example embodiment, the method includes placing a protective device, in a collapsed state, proximate to an opening to an internal channel of a subject. The device includes a first end portion, having a first diameter, that defines a first opening, and a second end portion, opposite the first end portion, having a second diameter and defining a second opening that is in communication with the first opening. The device also includes a body portion defined between the first end portion and second end portion. The body portion defines an interior passage between the first opening and second opening. The body portion is expandable, along a longitudinal axis, from a collapsed state to an expanded state. The method also includes expanding, into the internal channel of the subject, the body portion of the device from the collapsed state to the expanded state.

In yet another aspect, the present disclosure relates to a device for protecting an internal channel of a subject that, in one example embodiment, includes a first end portion having a first diameter and defining a first opening, and a second end portion, opposite the first end portion, having a second diameter that is less than the first diameter. The second end portion defines a second opening that is in communication with the first opening. The device also includes a body portion defined between the first end portion and second end portion, defining an interior passage between the first opening and second opening. The body portion is expandable, along a longitudinal axis, from a collapsed state to an expanded state and is formed with a substantially flexible material.

According to one example embodiment of the present disclosure, a protective device is placed, in a collapsed state, proximate an opening to an internal channel of a subject. The protective device has a first end portion, an opposite, second end portion, and a body portion defined between the first end portion and second end portion. The first end portion has a first diameter and defines a first opening, and the second end portion, which is opposite the first end portion, has a second diameter that may be less than the first diameter, and defines a second opening. The body portion defines an interior passage between the first opening and second opening.

The body portion is expandable along a longitudinal axis from a collapsed state to an expanded state. The protective device is positioned in the internal channel of the subject by expanding, into the internal channel of the subject, the body portion from the collapsed state to the expanded state. The body portion can be expanded from the collapsed state to the expanded state by engaging a tab disposed proximate the second end portion of the protective device. The tab can be grasped with a medical instrument having grasping capability and, using the instrument, the device can then be expanded from the collapsed state to the expanded state by pushing the second end portion into the internal channel of the subject such that the first end portion of the protective device extends at least partially outside of an opening to the internal channel of the subject and the second end portion is disposed at least partially inside the internal channel of the subject. The opening to the internal channel of the subject can include one or more portions of the nostril and nasal passages and cavities.

The body portion of the protective device can be formed with a flexible material such that, when placed in the internal channel of the subject, the body portion can conform to one or more contours of the internal channel. The size of the first diameter and size of the second diameter are specifically selected such that one or more medical instruments can pass through the interior passage defined by the body portion, for instance medical instruments used in performing surgical procedures at the skull base of a human subject. The first diameter can be greater than the second diameter such that the body portion of the protective device, when expanded, is substantially funnel-shaped along a longitudinal axis. One or both of the first end portion and second end portion can be formed to have an annular shape.

Other aspects and features of embodiments of the present disclosure will become apparent to those of ordinary skill in the art, upon reviewing the following detailed description in conjunction with the accompanying figures.

BRIEF DESCRIPTION OF THE DRAWINGS

FIG. 1A provides a front view illustration of the device in a collapsed state, FIG. 1B provides a side view illustration of the device in the collapsed state, and FIG. 1C provides a side view illustration of the device in an expanded state.

FIG. 3A provides a side, cross-sectional view of the device in a collapsed state and prior to placement in a nasal passage of the human subject. FIG. 3B provides a side, cross-sectional view of the device in an expanded state, placed in a nasal passage of the human subject, and a medical instrument passing through the interior passage of the body portion of the device.

DETAILED DESCRIPTION

Figure 1A:
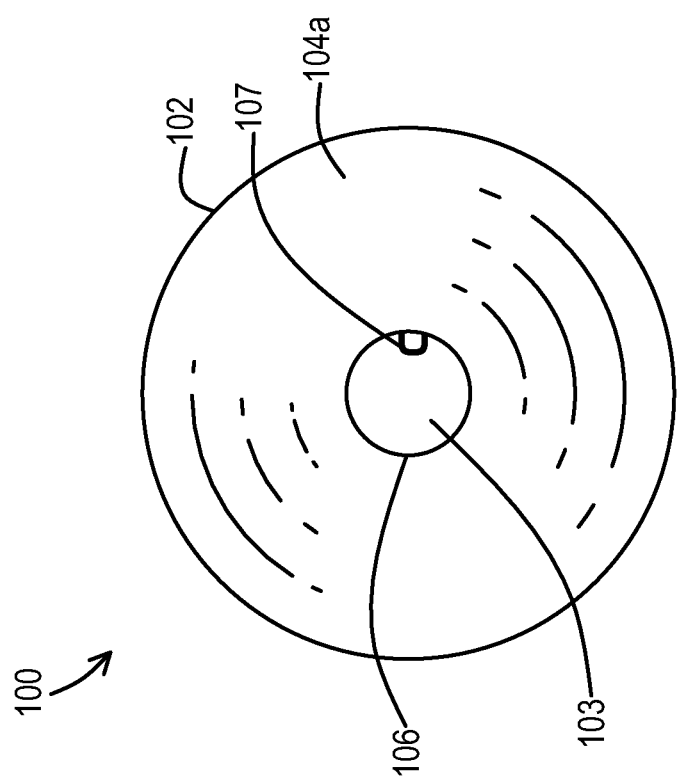
FIGS. 1A, 1B, and 1C are diagrams illustrating a device for protecting an internal channel of a subject, according to one example embodiment of the present disclosure.

Although example embodiments of the present disclosure are explained in detail, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more steps of a method does not preclude the presence of additional method steps or intervening method steps between those steps expressly identified. Method steps may be performed in a different order than those described herein. Similarly, it is also to be understood that the mention of one or more components in a device or system does not preclude the presence of additional components or intervening components between those components expressly identified.

Ranges may be expressed herein as from "about" or "approximately" one particular value and/or to "about" or "approximately" another particular value. When such a range is expressed, another embodiment includes from the one particular value and/or to the other particular value. As used herein, "about" or "approximately" means within 20 percent or closer of a given value or range.

In describing example embodiments, terminology will be resorted to for the sake of clarity. It is intended that each term contemplates its broadest meaning as understood by those skilled in the art and includes all technical equivalents that operate in a similar manner to accomplish a similar purpose.

As discussed herein, a "subject" or "patient" may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g. rat, dog, pig, monkey), etc. It should be appreciated that the subject may be any applicable human patient, for example.

The following detailed description is directed to devices and related methods for protecting an internal channel of a subject. In the following detailed description, references are made to the accompanying drawings that form a part hereof and that show, by way of illustration, specific embodiments or examples. In referring to the drawings, like numerals represent like elements throughout the several figures.

Figure 1B:
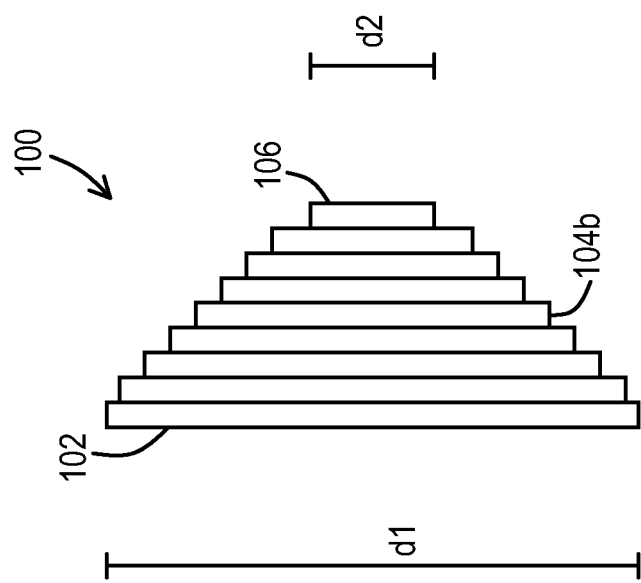
Figure 1C:
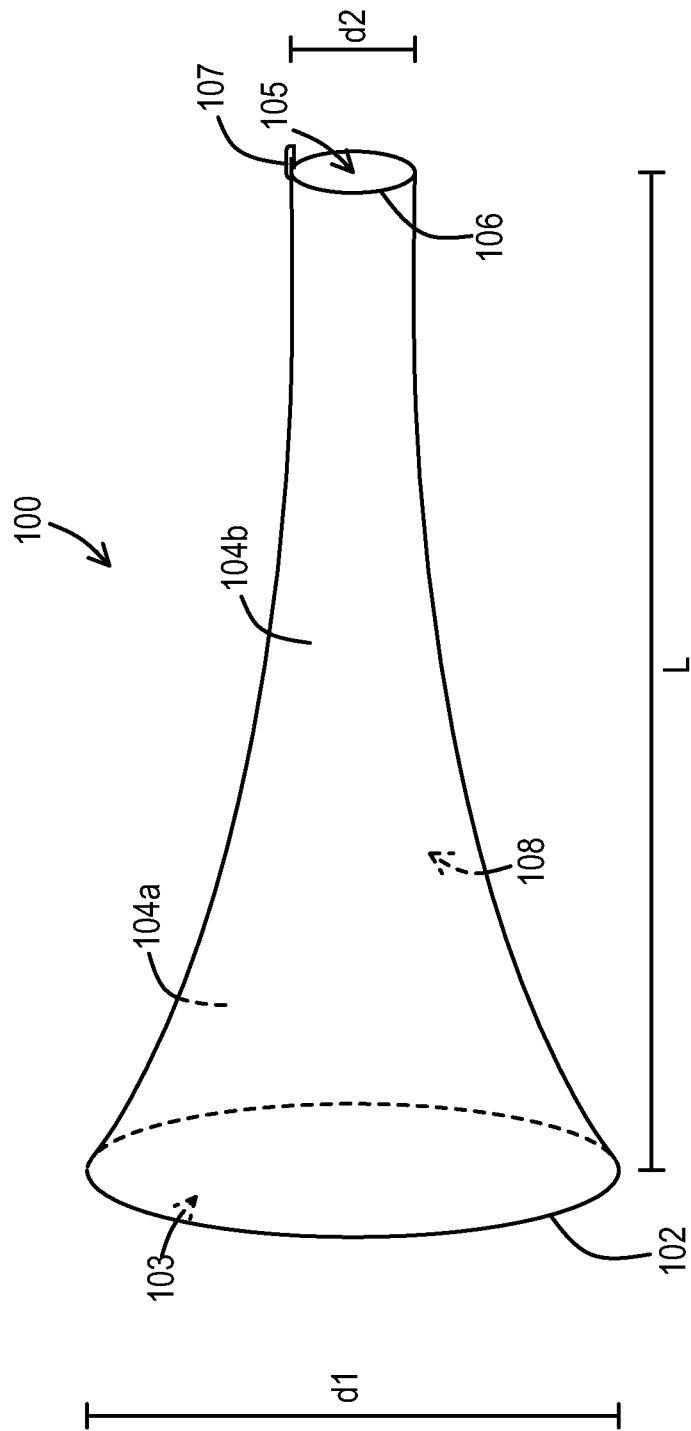

Example embodiments of devices and methods according to aspects of the present disclosure will now be described specifically with reference to FIGS. 1-3 of the drawings. FIGS. 1A, 1B, and 1C illustrate a device 100 according to an example embodiment of the present disclosure, where FIG. 1A is a diagram illustrating a front view of the device 100 in a collapsed state, FIG. 1B is a diagram illustrating a side view of the device 100 in the collapsed state, and FIG. 1C is a diagram illustrating a side view of the device 100 in an expanded state. As shown, the device 100 includes a first end portion 102 with a diameter $d_1$, defining a first opening 103. A second end portion 106 opposite the first end portion 102 has a second diameter $d_2$ that is less than the first diameter $d_1$. The second end portion 106 defines a second opening 105. A body portion 104, having an external wall 104b and internal wall 104a, is defined between the first end portion 102 and second end portion 106. A hollow interior passage 108 is created within the walls 104a, 104b of the body portion 104, from the first opening 103 to the second opening 105, such that the first opening 103 is in communication with the second opening 105. The body portion 104 is formed of a substantially flexible material such as to be expandable from a collapsed state (FIGS. 1A, 1B) to an expanded state (FIG. 1C) and such that the body portion 104 can conform to contours of an internal channel of a subject. The first end portion 102, second end portion 106, and body portion 104 can be configured such that the device can selectively collapse and expand in an accordion-like manner along the longitudinal axis.

As shown in FIG. 1C, in the expanded state, the body portion 104 is funnel-shaped along a longitudinal axis with a length L in a range from about 4-12 cm. The first end portion 102 and second end portion 106 are each annular in shape and can be formed with rigid or semi-rigid portions. The device 100 also includes a tab 107 that is disposed proximate the second end portion 106 and configured to engage with an instrument to expand the body portion 104 from the collapsed state to the expanded state. As shown in further detail in the illustrations of FIGS. 2 and 3A-3B, the first diameter $d_1$ and second diameter $d_2$ are sized such as to permit one or more medical instruments to pass through the interior passage 108 defined by the body portion 104 of the device 100. For example, an endoscope (not shown) may be passed through the interior passage 108 for a medical procedure performed in an area proximate the skull base of a human subject. The first diameter $d_1$ may be in a range from about 2-3 cm and the second diameter $d_2$ may be in a range from about 1-2 cm.

Figure 2:
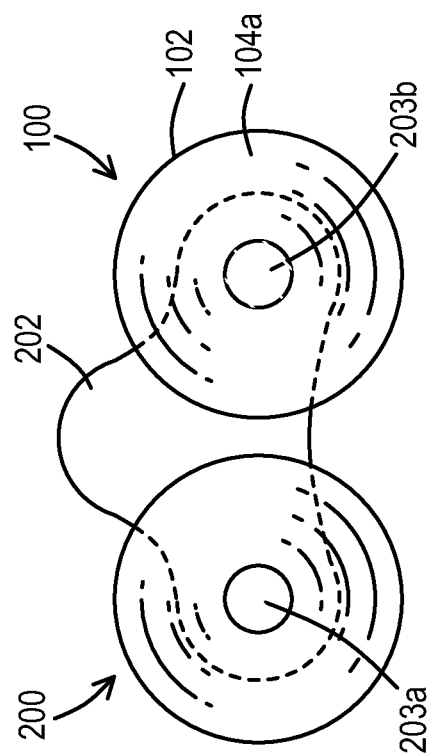
FIG. 2 is a diagram illustrating a front view of a device according to the example embodiment illustrated in FIGS. 1A-1C, placed in each nostril of a human subject.
Figure 3A:
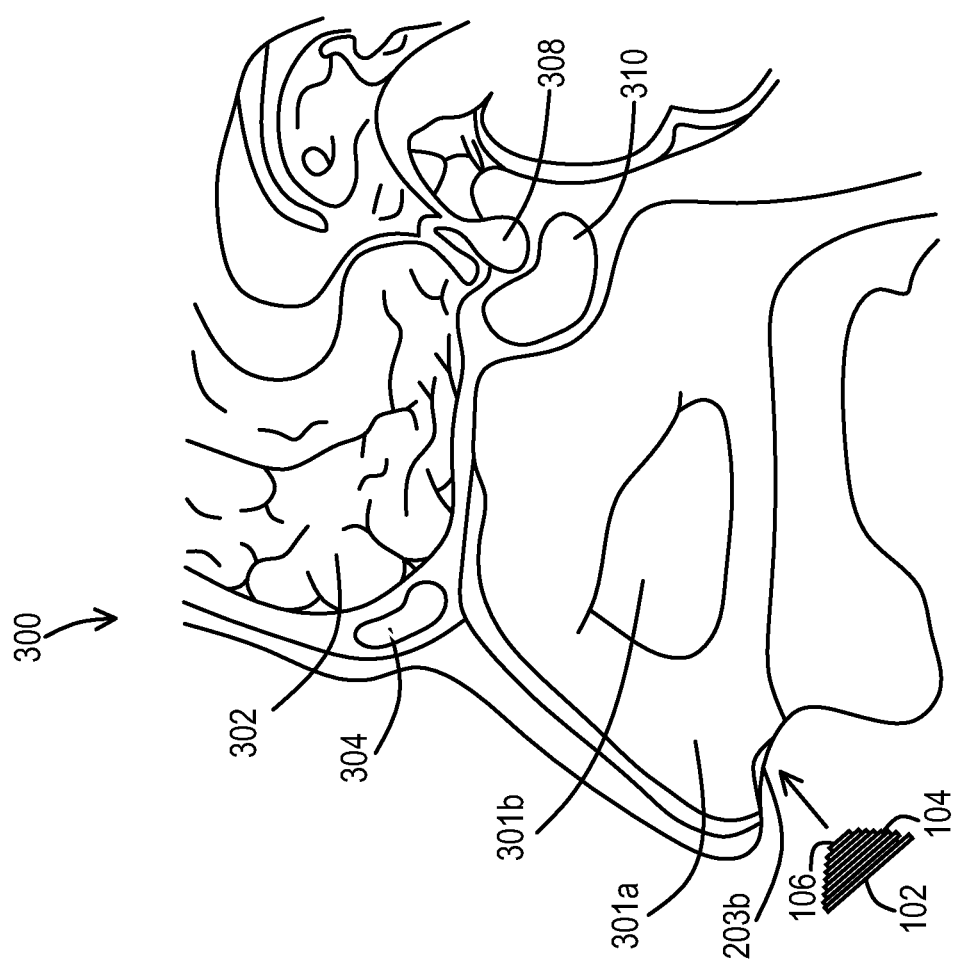
FIGS. 3A and 3B are diagrams providing side, cross-sectional views of a device in accordance with the example embodiment shown in FIGS. 1A-1C being implemented in a medical procedure performed in an area proximate the skull base of a human subject, according to example embodiments of the present disclosure.
Figure 3B:
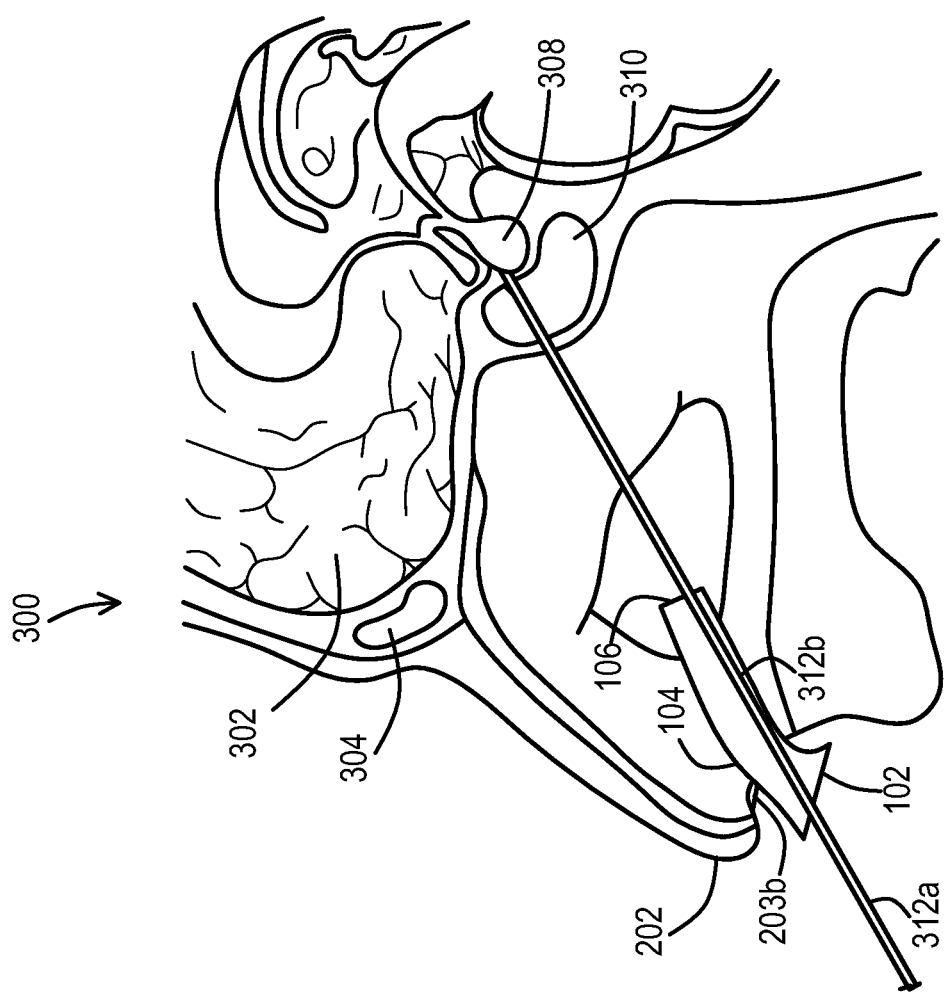

The diagram of FIG. 2 illustrates a front view of a device 100 and a device 200, each structured according to the example embodiment illustrated in FIGS. 1A-1C, placed in the nostrils 203a, 203b of the nose 202 of a human subject 300. FIGS. 3A and 3B are diagrams providing side, cross-sectional views of the device 100 in accordance with the example embodiment shown in FIGS. 1A-1C being implemented in a medical procedure performed in an area proximate the skull base of the human subject 300, according to example embodiments of the present disclosure. FIG. 3A provides a side, cross-sectional view of the device 100 in a collapsed state and prior to placement in an internal channel 301 of the human subject 300, which includes portions of the nostrils 203a, 203b and nasal passages and cavities 301a, 301b inside the nose 202. FIG. 3B provides a side, cross-sectional view of the device 100 in an expanded state and placed in the internal channel 301 of the subject 300.

A medical instrument 312 passes through the interior passage 108 defined by the body portion 104 of the device 100, where a first portion 312a of the medical instrument 312 is disposed outside of the internal channel 301 and the second portion 312b is disposed inside the internal channel 301. As shown in FIG. 3B, when the body portion 104 of the device 100 is disposed in the internal channel 301 of the subject 300, the first end portion 102 extends outside the nose 202 and the second end portion 106 is disposed in the internal channel 301. In the particular example shown in FIG. 3B, the device 100 is being implemented in a transphenoidal surgical procedure in which the medical instrument 312 is a curette that is passed through the interior passage 108 of the device 100, thereby passing through the internal channel 301, to the sphenoid cavity 310 and pituitary gland 308. For reference, portions of the brain 302 and frontal sinus 304 are also shown.

As a further example of practicing concepts and technologies presented herein in accordance with aspects of the present disclosure, a protective device in accordance with the example embodiment described above with respect to FIG. 1 is placed in each nasal cavity of a subject, to allow easy passage of both endoscopes and instruments through the nasal cavity and into the sphenoid sinus/pituitary sella. After the initial approach to the sphenoid sinus and either immediately before or after removing the face of the pituitary sella, the protective device is placed in each of the subject's nostrils. The device remains in place until the conclusion of the procedure, at which point it may be removed, or alternatively it may be left in place for a predetermined duration (for example 24-48 hours) to serve as a temporary stent to prevent early adhesion formation. Use of the protective device may prevent nasal trauma, post-operative congestion, nasal synechia, and sinusitis. By providing a protective barrier for the inside of the nose, a medical professional may more easily and quickly guide instruments in and out of the nose without risk of mucosal injury. Also, use of the protective device may reduce the need for scope washing and post-operative packing materials.

Those skilled in the art will recognize that instruments passed through protective devices according to aspects of the present disclosure can include any standard instruments used in a medical procedure associated with the skull base, for example endoscopes, grasping devices, cutting devices, and cauterizing devices. It should also be appreciated that the protective devices and related methods described herein can be implemented in medical procedures other than transnasal procedures, such as those relating to the ear or throat.

Numerous characteristics and advantages have been set forth in the foregoing description, together with details of structure and function. While the present disclosure has been disclosed in several forms, it will be apparent to those skilled in the art that many modifications, additions, and deletions, especially in matters of shape, size, and arrangement of parts, can be made therein without departing from the spirit and scope of the disclosure and its equivalents as set forth in the following claims. Therefore, other modifications or embodiments as may be suggested by the teachings herein are particularly reserved as they fall within the breadth and scope of the claims here appended.

What is claimed is:

1. A device for protecting an internal channel of a subject, comprising:
   a first end portion having a first diameter and defining a first opening;
   a second end portion, opposite the first end portion, having a second diameter that is less than the first diameter and defining a second opening that is in communication with the first opening; and
   a body portion defined between the first end portion and second end portion and defining an interior passage between the first opening and second opening, wherein the body portion is configured to expand in a longitudinal direction from a collapsed state to an expanded state to extend in length, wherein the second diameter is less than the first diameter when the body portion is in the expanded state and the second end portion is at least partially inside the internal channel of the subject, wherein the internal channel of the subject corresponds to a nasal passage of the subject, and
   wherein the second end portion is configured to selectively engage an instrument for pushing the second end portion into the internal channel of the subject to expand the body portion in the longitudinal direction from the collapsed state to the expanded state such that the first end portion extends at least partially outside of an opening to the internal channel of the subject and the second end portion is at least partially inside the internal channel of the subject.

2. The device of claim 1, wherein the first diameter and the second diameter are selected such as to permit at least one medical instrument to pass through the interior passage of the body portion.

3. The device of claim 2, wherein the at least one medical instrument is associated with a procedure performed in an area proximate a skull base of the subject.

4. The device of claim 1, wherein the body portion is formed with a substantially flexible material.

5. The device of claim 1, comprising a tab separate from the body portion and disposed at the second end portion, configured to engage with the instrument for expanding the body portion in the longitudinal direction from the collapsed state to the expanded state.

6. The device of claim 1, wherein the body portion is substantially funnel-shaped in the longitudinal direction.

7. The device of claim 1, wherein at least one of the first end portion and second end portion is substantially annular in shape.

8. The device of claim 1, wherein the opening to the internal channel of the subject corresponds to a nostril of the subject.

9. A method for protecting an internal channel of a subject, comprising:
   placing a protective device, in a collapsed state, proximate to an opening to an internal channel of a subject corresponding to a nostril of the subject, wherein the protective device comprises:
      a first end portion having a first diameter and defining a first opening,
      a second end portion, opposite the first end portion, having a second diameter that is less than the first diameter and defining a second opening that is in communication with the first opening, and a body portion defined between the first end portion and second end portion and defining an interior passage between the first opening and second opening, wherein the body portion is configured to expand in a longitudinal direction from a collapsed state to an expanded state to extend in length; and selectively engaging an instrument with the second end portion for expanding, into the internal channel of the subject, the body portion along the longitudinal axis from the collapsed state to the expanded state, wherein the second diameter is less than the first diameter when the body portion is in the expanded state and the second end portion is at least partially inside the internal channel of the subject, and wherein expanding the body portion from the collapsed state to the expanded state comprises pushing the second end portion into the internal channel of the subject such that the first end portion extends at least partially outside of the opening to the internal channel of the subject and the second end portion is disposed at least partially inside the internal channel of the subject.

10. The method of claim 9, wherein engaging the instrument with the second end portion for expanding the body portion from the collapsed state to the expanded state comprises engaging the instrument with a tab separate from the body portion and disposed at the second end portion of the protective device.

11. The method of claim 9, wherein the body portion is formed with a substantially flexible material.

12. The method of claim 11, wherein at least one of the first diameter, second diameter, and substantially flexible material are selected such that, when placed in an internal channel of a subject, the body portion substantially conforms to a contour of the internal channel of the subject.

13. The method of claim 12, wherein the first diameter and second diameter are selected such as to permit at least one medical instrument to pass through the interior passage defined by the body portion.

14. The method of claim 13, wherein the at least one medical instrument is associated with a procedure performed in an area proximate a skull base of a subject.

15. The method of claim 9, wherein the internal channel of the subject corresponds to a nasal passage of the subject.

16. The method of claim 9, wherein the body portion is substantially funnel-shaped along the longitudinal axis.

17. The method of claim 9, wherein at least one of the first end portion and second end portion is substantially annular in shape.

18. A device for protecting an internal channel of a subject, comprising:

a first end portion having a first diameter and defining a first opening;

a second end portion, opposite the first end portion, having a second diameter that is less than the first diameter and defining a second opening that is in communication with the first opening; and a body portion defined between the first end portion and second end portion and defining an interior passage between the first opening and second opening, wherein the body portion is formed with a substantially flexible material and is configured to expand in a longitudinal direction from a collapsed state to an expanded state to extend in length, wherein the second diameter is less than the first diameter when the body portion is in the expanded state and the second end portion is at least partially inside the internal channel of the subject, wherein the internal channel of the subject corresponds to a nasal passage of the subject, and wherein the second end portion is configured to selectively engage an instrument for pushing the second end portion into the internal channel of the subject to expand the body portion in the longitudinal direction from the collapsed state to the expanded state such that the first end portion extends at least partially outside of an opening to the internal channel of the subject and the second end portion is at least partially inside the internal channel of the subject.

19. The device of claim 18, wherein the first diameter and second diameter are selected such as to permit at least one medical instrument to pass through the interior passage defined by the body portion.

20. The device of claim 19, wherein the at least one medical instrument is associated with a procedure performed in an area proximate a skull base of a subject.

21. The device of claim 19, wherein the at least one medical instrument includes an endoscope.

22. The device of claim 18, wherein at least one of the first diameter, second diameter, and substantially flexible material are selected such that, when placed into the internal channel of a subject, the body portion substantially conforms to a contour of the internal channel of the subject.

23. The device of claim 18, comprising a tab separate from the body portion and disposed at the second end portion, configured to engage with the instrument for expanding the body portion in the longitudinal direction from the collapsed state to the expanded state.

24. The device of claim 18, wherein the body portion is substantially funnel-shaped in the longitudinal direction.

25. The device of claim 18, wherein at least one of the first end portion and second end portion is substantially annular in shape.

26. The device of claim 18, wherein the opening to the internal channel of the subject corresponds to a nostril of the subject.

* * * * *